(12) United States Patent
Venkatadri et al.

(10) Patent No.: US 11,628,275 B2
(45) Date of Patent: Apr. 18, 2023

(54) ELECTRONIC DEVICES

(71) Applicant: ANALOG DEVICES, INC., Norwood, MA (US)

(72) Inventors: Vikram Venkatadri, Malden, MA (US); David Frank Bolognia, Charlestown, MA (US)

(73) Assignee: ANALOG DEVICES, INC., Norwood, MA (US)

( * ) Notice: Subject to any disclaimer, the term of this patent is extended or adjusted under 35 U.S.C. 154(b) by 1002 days.

(21) Appl. No.: 16/261,333

(22) Filed: Jan. 29, 2019

(65) Prior Publication Data
US 2019/0232021 A1 Aug. 1, 2019

Related U.S. Application Data

(60) Provisional application No. 62/624,669, filed on Jan. 31, 2018.

(51) Int. Cl.
A61B 5/05 (2021.01)
A61M 25/01 (2006.01)
A61B 5/06 (2006.01)

(52) U.S. Cl.
CPC ......... *A61M 25/0127* (2013.01); *A61B 5/062* (2013.01); *A61B 2562/164* (2013.01); *A61M 2025/0166* (2013.01)

(58) Field of Classification Search
CPC combination set(s) only.
See application file for complete search history.

(56) References Cited

U.S. PATENT DOCUMENTS

| 3,724,274 A | 4/1973 | Millar |
| 3,949,274 A | 4/1976 | Anacker |
| 4,006,394 A | 2/1977 | Cuda |
| 4,742,183 A | 5/1988 | Soloway et al. |

(Continued)

FOREIGN PATENT DOCUMENTS

| CN | 102129053 | 7/2011 |
| CN | 202393897 | 8/2012 |

(Continued)

OTHER PUBLICATIONS

Extended European Search Report issued in application No. 19154358.6 dated Oct. 9, 2019.

(Continued)

*Primary Examiner* — Joel F Brutus
(74) *Attorney, Agent, or Firm* — Knobbe, Martens, Olson & Bear, LLP

(57) ABSTRACT

An electronic device is disclosed. The electronic device comprise an elongate electrical connector that is configured to connect to an integrated device package. The elongate electrical connector can comprise an elongate flexible substrate. The elongate flexible substrate has a proximal portion and a distal portion spaced from the proximal portion by a length along a longitudinal axis. The elongate flexible substrate has a width along an axis transverse to the longitudinal axis. The elongate flexible substrate defines an elongation ratio of the length to the width. The elongation ratio is at least 100:1. The elongate electrical connector can be connected to a bobbin. The elongate electrical connector can be configured to unspool from the bobbin.

20 Claims, 12 Drawing Sheets

(56) References Cited

U.S. PATENT DOCUMENTS

| | | |
|---|---|---|
| 4,928,206 A | 5/1990 | Porter |
| 5,074,863 A | 12/1991 | Dines |
| 5,126,286 A | 6/1992 | Chance |
| 5,289,122 A | 2/1994 | Shigeno |
| 5,405,337 A | 4/1995 | Maynard |
| 5,452,182 A | 9/1995 | Eichelberger et al. |
| 5,554,806 A | 9/1996 | Mizuno et al. |
| 5,555,159 A | 9/1996 | Dore |
| 5,616,863 A | 4/1997 | Koen |
| 5,644,230 A | 7/1997 | Pant et al. |
| 5,731,222 A | 3/1998 | Malloy et al. |
| 5,833,608 A | 11/1998 | Acker |
| 5,903,440 A | 5/1999 | Blazier et al. |
| 6,040,624 A | 3/2000 | Chambers et al. |
| 6,052,610 A | 4/2000 | Koch |
| 6,075,708 A | 6/2000 | Nakamura |
| 6,078,102 A | 6/2000 | Crane, Jr. et al. |
| 6,097,183 A | 8/2000 | Goetz et al. |
| 6,106,476 A | 8/2000 | Corl et al. |
| 6,169,254 B1 | 1/2001 | Pant et al. |
| 6,184,680 B1 | 2/2001 | Shinoura et al. |
| 6,225,688 B1 | 5/2001 | Kim |
| 6,278,271 B1 | 8/2001 | Schott |
| 6,291,894 B1 | 9/2001 | Farnworth et al. |
| 6,304,082 B1 | 10/2001 | Gualtieri et al. |
| 6,326,908 B1 | 12/2001 | Hoffman et al. |
| 6,339,191 B1 | 1/2002 | Crane, Jr. et al. |
| 6,348,427 B1 | 2/2002 | Hamada et al. |
| 6,511,863 B2 | 1/2003 | Farnworth et al. |
| 6,536,123 B2 | 3/2003 | Tamura |
| 6,570,246 B1 | 5/2003 | Lee et al. |
| 6,591,492 B2 | 7/2003 | Farrar |
| 6,705,005 B1 | 3/2004 | Blazier et al. |
| 6,721,189 B1 | 4/2004 | Haba |
| 6,777,261 B2 | 8/2004 | Farnworth et al. |
| 6,784,659 B2 | 8/2004 | Haji-Sheikh et al. |
| 6,852,607 B2 | 2/2005 | Song et al. |
| 6,903,465 B2 | 6/2005 | Farnworth et al. |
| 6,993,443 B2 | 1/2006 | Haerle |
| 6,993,974 B2 | 2/2006 | Tenerz et al. |
| 7,012,812 B2 | 3/2006 | Haba |
| 7,115,984 B2 | 10/2006 | Poo et al. |
| 7,202,552 B2 | 4/2007 | Zhe et al. |
| 7,211,886 B2 | 5/2007 | Hsu et al. |
| 7,265,719 B1 | 9/2007 | Moosbrugger et al. |
| 7,301,332 B2 | 11/2007 | Govari et al. |
| 7,307,415 B2 | 12/2007 | Seger et al. |
| 7,375,009 B2 | 5/2008 | Chua et al. |
| 7,408,342 B2 | 8/2008 | Desplats et al. |
| 7,408,343 B2 | 8/2008 | Dmytriw et al. |
| 7,420,262 B2 | 9/2008 | Bauer et al. |
| 7,429,788 B2 | 9/2008 | Clayton et al. |
| 7,467,552 B2 | 12/2008 | MacGugan |
| 7,525,309 B2 | 4/2009 | Sherman et al. |
| 7,812,596 B2 | 10/2010 | Potter et al. |
| 7,839,657 B2 | 11/2010 | Nodine |
| 8,095,223 B2 | 1/2012 | Cleary et al. |
| 8,115,480 B2 | 2/2012 | Masubuchi et al. |
| 8,134,361 B2 | 3/2012 | Azumi et al. |
| 8,148,978 B2 | 4/2012 | Sherman et al. |
| 8,421,453 B2 | 4/2013 | Bauer |
| 8,692,366 B2 | 4/2014 | Xue et al. |
| 8,750,961 B1 | 6/2014 | Ries et al. |
| 8,786,278 B2 | 7/2014 | Ohta et al. |
| 8,836,132 B2 | 9/2014 | Xue |
| 8,957,679 B2 | 2/2015 | Loreit et al. |
| 9,000,763 B2 | 4/2015 | Ausserlechner |
| 9,030,194 B2 | 5/2015 | Dolsak |
| 9,069,033 B2 | 6/2015 | Chen et al. |
| 9,093,360 B2 | 7/2015 | Bologna |
| 9,103,657 B2 | 8/2015 | Ruigrok et al. |
| 9,116,022 B2 | 8/2015 | Bologna |
| 9,234,736 B2 | 1/2016 | Engel et al. |
| 9,268,001 B2 | 2/2016 | Ausserlechner |
| 9,278,851 B2 | 3/2016 | Xue |
| 9,286,924 B1 | 3/2016 | Akatsuka et al. |
| 9,297,863 B2 | 3/2016 | Jeng et al. |
| 9,332,940 B1 | 5/2016 | Bologna |
| 9,335,149 B2 | 5/2016 | Stark |
| 9,372,064 B2 | 6/2016 | Zwijze et al. |
| 9,470,552 B2 | 10/2016 | Ausserlechner |
| 9,475,694 B2 | 10/2016 | Martizon, Jr. et al. |
| 9,494,661 B2 | 11/2016 | Paul et al. |
| 9,513,344 B2 | 12/2016 | Ausserlechner |
| 9,601,455 B2 | 3/2017 | Nishiyama et al. |
| 9,624,095 B2 | 4/2017 | Millett et al. |
| 9,625,276 B2 | 4/2017 | Ausserlechner |
| 9,658,298 B2 | 5/2017 | Cai et al. |
| 9,780,471 B2 | 10/2017 | Van Rijswijk |
| 9,877,660 B2 | 1/2018 | O'Connell et al. |
| 9,895,053 B2 | 2/2018 | Fujimori et al. |
| 9,941,237 B2 | 4/2018 | Nishiyama et al. |
| 9,995,600 B2 | 6/2018 | Nagarkar et al. |
| 10,081,266 B2 | 9/2018 | Draeger et al. |
| 10,201,311 B2 | 2/2019 | Chou et al. |
| 10,281,710 B2 | 5/2019 | Fujimori |
| 10,337,888 B2 | 7/2019 | Jost et al. |
| 2002/0005715 A1 | 1/2002 | Sato |
| 2002/0077752 A1 | 6/2002 | Burreson et al. |
| 2002/0180605 A1 | 12/2002 | Ozguz et al. |
| 2003/0120150 A1 | 6/2003 | Govari |
| 2003/0146332 A1 | 8/2003 | Vinding |
| 2003/0209789 A1 | 11/2003 | Hanson et al. |
| 2004/0157410 A1 | 8/2004 | Yamaguchi |
| 2004/0169244 A1 | 9/2004 | MacGugan |
| 2005/0184187 A1 | 8/2005 | Ullman et al. |
| 2005/0230795 A1 | 10/2005 | Furuyama et al. |
| 2006/0082363 A1 | 4/2006 | Ricks et al. |
| 2006/0129061 A1 | 6/2006 | Kaneto et al. |
| 2006/0151864 A1 | 7/2006 | Anderson et al. |
| 2006/0261453 A1 | 11/2006 | Lee et al. |
| 2007/0035294 A1 | 2/2007 | Peczalski et al. |
| 2007/0053504 A1 | 3/2007 | Sato et al. |
| 2007/0249901 A1* | 10/2007 | Ohline .................. A61B 5/068 600/117 |
| 2008/0175425 A1 | 7/2008 | Roberts et al. |
| 2008/0285111 A1 | 11/2008 | Ishii et al. |
| 2009/0027048 A1 | 1/2009 | Sato et al. |
| 2009/0121342 A1 | 5/2009 | Minakawa et al. |
| 2009/0243402 A1 | 10/2009 | O'Day et al. |
| 2009/0268019 A1 | 10/2009 | Ishii |
| 2009/0295381 A1 | 12/2009 | Theuss et al. |
| 2009/0315554 A1 | 12/2009 | Witcraft et al. |
| 2010/0072992 A1 | 3/2010 | Bauer |
| 2010/0078739 A1 | 4/2010 | Xue et al. |
| 2010/0090295 A1 | 4/2010 | Zhe et al. |
| 2010/0130923 A1 | 5/2010 | Cleary et al. |
| 2010/0155863 A1 | 6/2010 | Weekamp |
| 2010/0197148 A1 | 8/2010 | Rudisill et al. |
| 2010/0331635 A1 | 12/2010 | Wang |
| 2011/0018143 A1 | 1/2011 | Chua et al. |
| 2011/0074406 A1 | 3/2011 | Mather et al. |
| 2011/0149522 A1 | 6/2011 | Johann et al. |
| 2011/0227569 A1 | 9/2011 | Cai et al. |
| 2011/0234218 A1 | 9/2011 | Lagouge |
| 2011/0248706 A1 | 10/2011 | Davis et al. |
| 2012/0217960 A1 | 8/2012 | Ausserlechner |
| 2012/0256619 A1 | 10/2012 | Muto et al. |
| 2012/0268113 A1 | 10/2012 | Sato et al. |
| 2013/0023769 A1 | 1/2013 | Tsai et al. |
| 2013/0134969 A1 | 5/2013 | Ohta et al. |
| 2013/0249542 A1 | 9/2013 | Zhao et al. |
| 2013/0313130 A1 | 11/2013 | Little et al. |
| 2013/0320969 A1 | 12/2013 | Reichenbach et al. |
| 2013/0335072 A1 | 12/2013 | Malzfeldt |
| 2014/0005521 A1 | 1/2014 | Kohler et al. |
| 2014/0197531 A1 | 7/2014 | Bologna |
| 2014/0266187 A1 | 9/2014 | Mather |
| 2015/0066007 A1 | 3/2015 | Srivastava |
| 2015/0084619 A1 | 3/2015 | Stark |
| 2015/0141854 A1* | 5/2015 | Eberle ................ A61B 5/02154 600/488 |
| 2015/0164469 A1 | 6/2015 | Corl |
| 2015/0204950 A1 | 7/2015 | Ausserlechner |

(56) References Cited

U.S. PATENT DOCUMENTS

| | | |
|---|---|---|
| 2015/0285611 A1 | 10/2015 | Lowery et al. |
| 2016/0161288 A1 | 6/2016 | Lu |
| 2016/0169985 A1 | 6/2016 | Weber et al. |
| 2016/0178397 A1 | 6/2016 | Jost et al. |
| 2016/0249817 A1 | 9/2016 | Mazar et al. |
| 2017/0014198 A1 | 1/2017 | Gravlee |
| 2017/0108354 A1 | 4/2017 | Maiterth et al. |
| 2017/0136906 A1 | 5/2017 | Draeger et al. |
| 2017/0164867 A1 | 6/2017 | Kassab et al. |
| 2017/0276738 A1 | 9/2017 | Holm et al. |
| 2017/0356764 A1 | 12/2017 | Deak et al. |
| 2018/0021545 A1 | 1/2018 | Mitchell et al. |
| 2018/0062071 A1 | 3/2018 | Bolognia et al. |
| 2018/0113176 A1 | 4/2018 | Nagata et al. |
| 2018/0122784 A1 | 5/2018 | Bolognia |
| 2018/0128648 A1 | 5/2018 | Schmitt |
| 2018/0216967 A1 | 8/2018 | Sun et al. |
| 2018/0274896 A1 | 9/2018 | Anagawa et al. |

FOREIGN PATENT DOCUMENTS

| | | |
|---|---|---|
| CN | 202604785 U | 12/2012 |
| CN | 103038782 A | 4/2013 |
| CN | 103403627 A | 11/2013 |
| CN | 103622688 A | 3/2014 |
| CN | 103720461 A | 4/2014 |
| CN | 103826528 A | 5/2014 |
| CN | 103889308 A | 6/2014 |
| CN | 105452812 | 3/2016 |
| DE | 10 2011 001 422 A1 | 9/2012 |
| DE | 10 2017 125 732 A1 | 5/2018 |
| EP | 0 575 800 A2 | 12/1993 |
| EP | 0 575 800 A3 | 10/1996 |
| EP | 0 783 666 | 7/1997 |
| EP | 1 321 743 | 6/2003 |
| EP | 1 365 208 | 11/2003 |
| GB | 2528251 A | 1/2016 |
| JP | 09121015 A | 5/1997 |
| JP | 2002-022403 A | 1/2002 |
| JP | 2002-529133 A | 9/2002 |
| JP | 2008-305395 A | 12/2008 |
| JP | 2009-289724 A | 12/2009 |
| JP | 2010-258038 A | 11/2010 |
| JP | 2011-501163 A | 1/2011 |
| JP | 2011-220977 A | 11/2011 |
| JP | 2016-169685 A | 9/2016 |
| JP | 2018-072344 A | 5/2018 |
| WO | WO 96/10731 | 4/1996 |
| WO | WO 00/27281 | 5/2000 |
| WO | WO 01/04656 | 1/2001 |
| WO | WO 2002/052221 | 12/2001 |
| WO | WO 2009/052537 | 4/2009 |
| WO | WO 2011/080935 | 7/2011 |
| WO | WO 2016/020326 A1 | 2/2016 |
| WO | WO 2016/127130 A1 | 8/2016 |
| WO | WO 2016/171597 A1 | 10/2016 |

OTHER PUBLICATIONS

Extended European Search Report issued in application No. 20201398.3 dated Feb. 24, 2021.

Tanase et al., "Multi-parameter sensor system with intravascular navigation for catheter/guide wire application", Sensors and Actuators A 97-98:116-124 (2002).

Office Action received in CN 201910094402 dated Jan. 26, 2022.

Li, "Polymer Flip-chip Bonding of Pressure Sensors on Flexible Kapton Film for Neonatal Catheters", A thesis submitted to the Division of Research and Advanced Studies of the University of Cincinnati (2004).

Sensors—Harting Mitronics, Harting Pushing Performance, in 2 pages (downloaded from World Wide Web page: harting-mitronics. ch/en/produkte/anwendungen/sensorik/index.php on Jul. 11, 2011).

Images obtained on Jun. 13, 2011 from a web search related to three-dimensional packaging.

* cited by examiner

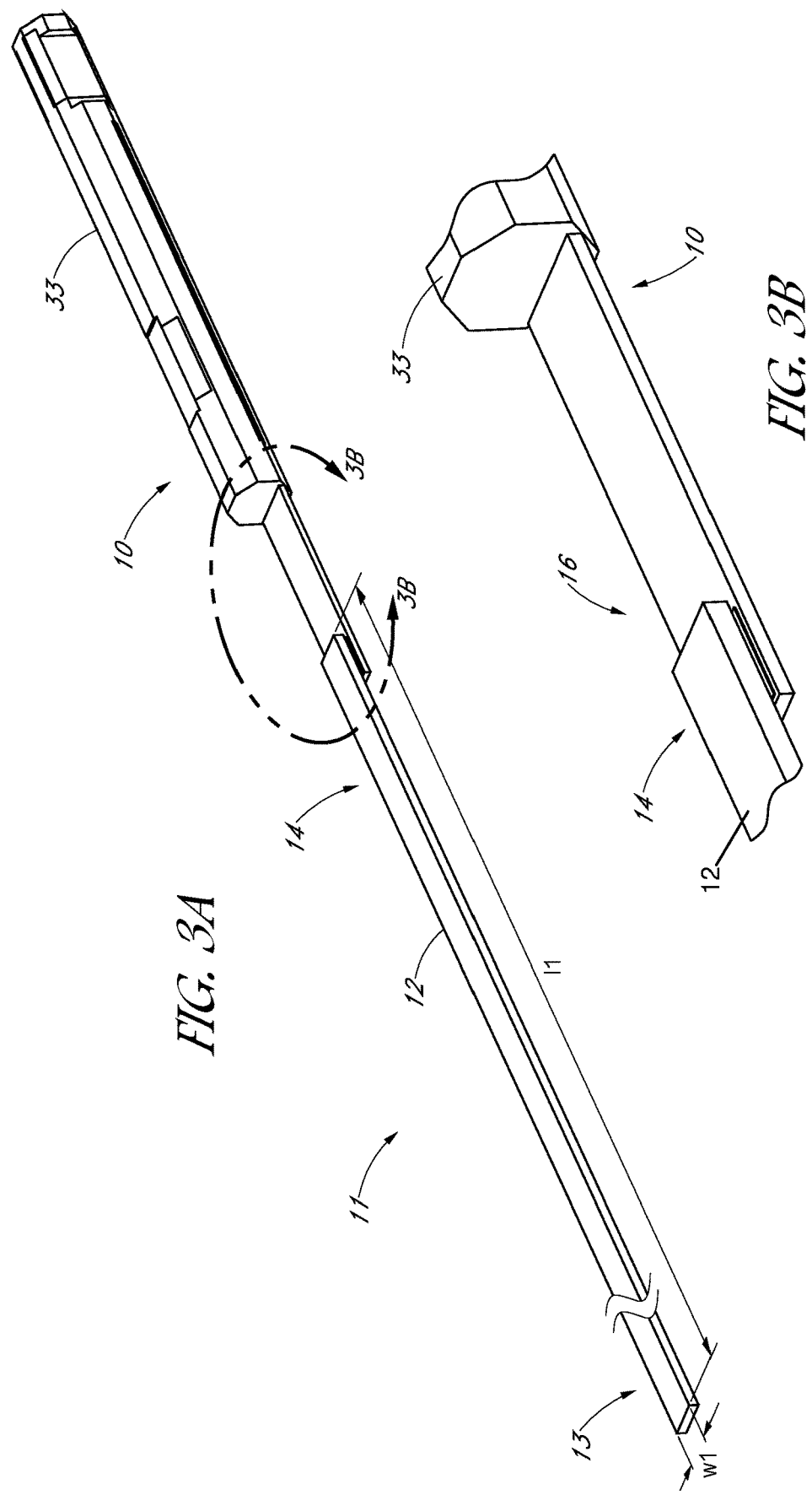

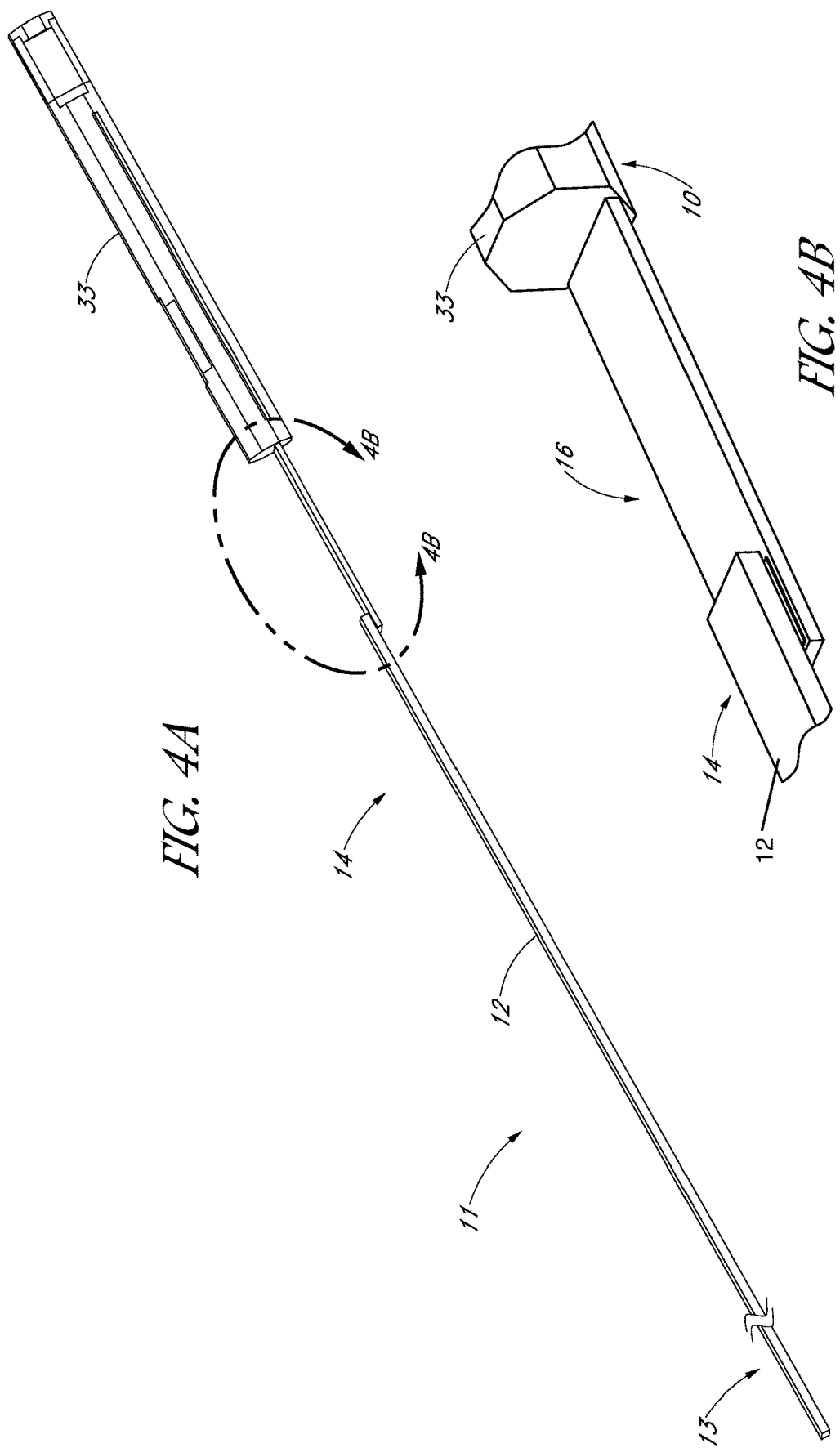

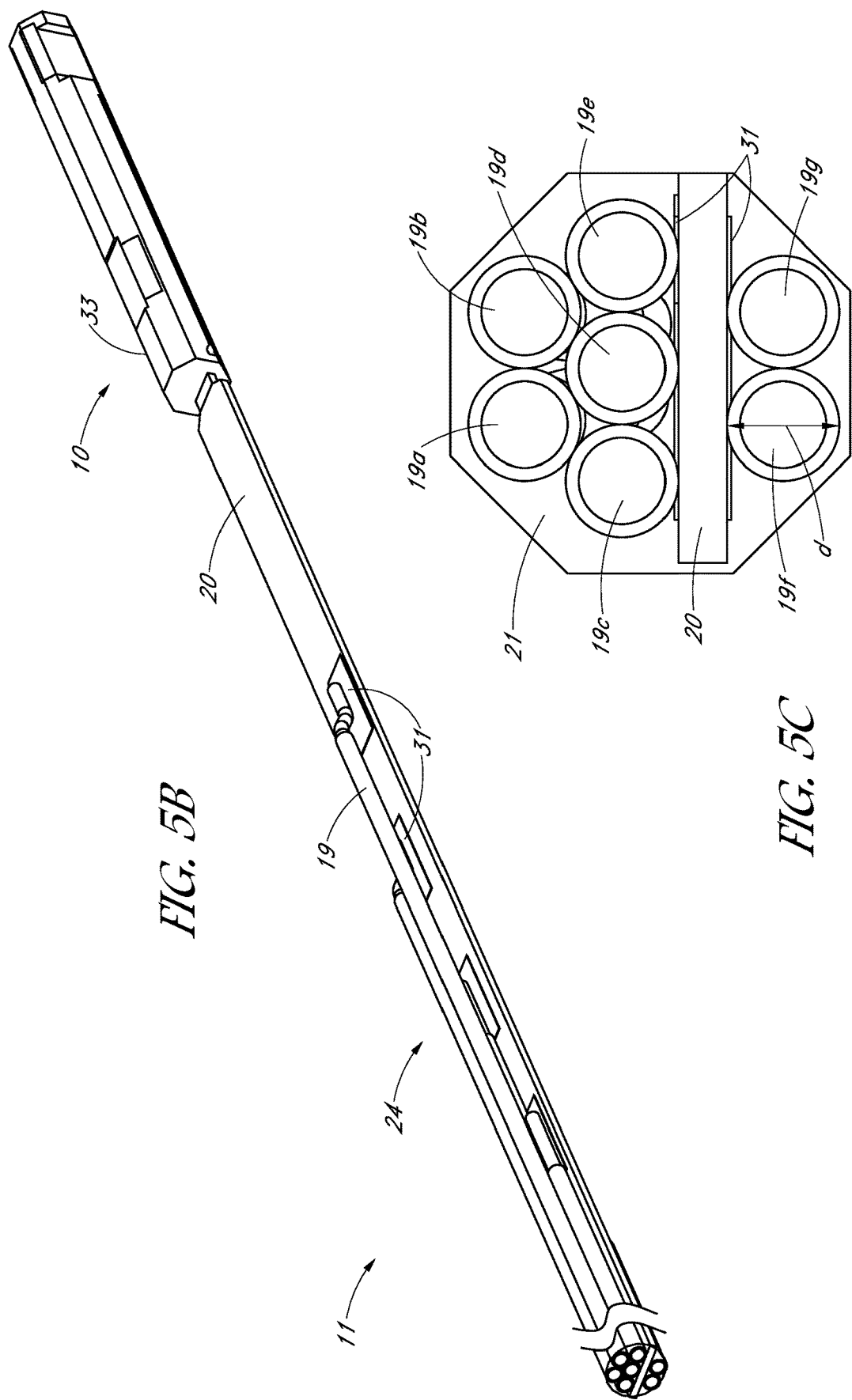

ELECTRONIC DEVICES

CROSS-REFERENCE TO RELATED APPLICATIONS

This application claims the benefit of U.S. Provisional Application No. 62/624,669 entitled "ELECTRONIC DEVICES," filed Jan. 31, 2018, the entire disclosure of which is incorporated herein by reference for all purposes.

BACKGROUND

Field

The field relates to electronic devices configured for use in a catheter lumen, such as for minimally invasive surgical or diagnostic operations in a patient.

Description of the Related Art

Many medical devices utilize a catheter or other elongate structure to access internal organs of a human patient. For example, in various treatment and diagnostic procedures, a clinician can insert a guidewire through a body lumen of the patient and can deliver a distal end of the guidewire to a location within the patient. In cardiac treatment procedures, such as stent delivery, percutaneous transluminal angioplasty, cardiac mapping and ablation, cardiac pumping, or other percutaneous procedures, the clinician can use the Seldinger technique to access the patient's vascular system (e.g., the femoral artery) for insertion of the guidewire. Once the guidewire is placed at the target location, the clinician can insert a catheter system or other elongate structure over the guidewire to guide the catheter system to the treatment site.

Since the treatment or diagnosis site may be remote from the insertion site, it can be challenging to monitor the location and/or orientation of the distal end of the guidewire and/or the working end of the catheter system. The small diameter of the patient's blood vessels can limit the maximum diameter of the catheter system, which in turn makes it challenging to incorporate sensor device dies and associated packaging structures. Similarly, the skilled artisan will recognize other applications in which very small tools or devices should be located with precision.

Furthermore, during a medical procedure, the electronic device (e.g., a sensor device or package) may be remote from a controller that controls the operation of the electronic device. It can be challenging to provide electrical communication with such remote devices for real-time control and/or sensing during a procedure.

Accordingly, there remains a continuing need for electronic devices, such as medical devices, that act upon or sense locations that are remote from the controller, which may be located outside the body of the patient.

SUMMARY

In one embodiment, an electronic device is disclosed. The electronic device can include an elongate flexible substrate having a proximal portion and a distal portion spaced from the proximal portion by a length along a longitudinal axis. The elongate flexible substrate can have a width along an axis transverse to the longitudinal axis. The elongate flexible substrate can define an elongation ratio of the length to the width, the elongation ratio being at least 100:1. An integrated device package can be mechanically and electrically connected to the distal portion of the elongate flexible substrate.

In another embodiment, an electronic device is disclosed. The electronic device can include a bobbin and an elongate electrical connector configured to unspool from the bobbin. The elongate electrical connector can have a distal portion and a proximal portion that mechanically couples to the bobbin. An integrated device package can be coupled with the distal portion of the elongate electrical connector.

In another embodiment, a method of operating an electronic device that includes an integrated device package coupled with a distal portion of an elongate electrical connector is disclosed. The method can include unspooling the elongate electrical connector from a bobbin, a proximal portion of the elongate electrical connector being coupled with the bobbin. The method can include guiding the integrated device package to a target location in a body cavity of a patient.

BRIEF DESCRIPTION OF THE DRAWINGS

FIG. 3A is a schematic isometric view of an integrated device package connected to an elongate electrical connector that comprises a flexible substrate.

FIG. 3B is a zoomed-in view of FIG. 3A near a connection between the integrated device package and the elongate electrical connector.

FIG. 4A is a schematic isometric view of an integrated device package connected to an elongate electrical connector that comprises a flexible substrate in another embodiment.

FIG. 4B is a zoomed-in view of FIG. 4A near a connection between the integrated device package and the elongate electrical connector.

FIG. 5B is a schematic isometric view of the integrated device package and the elongate electrical connector of FIG. 5A.

FIG. 5C is a cross sectional view of the elongate electrical connector of FIGS. 5A and 5B.

DETAILED DESCRIPTION

Figure 1:
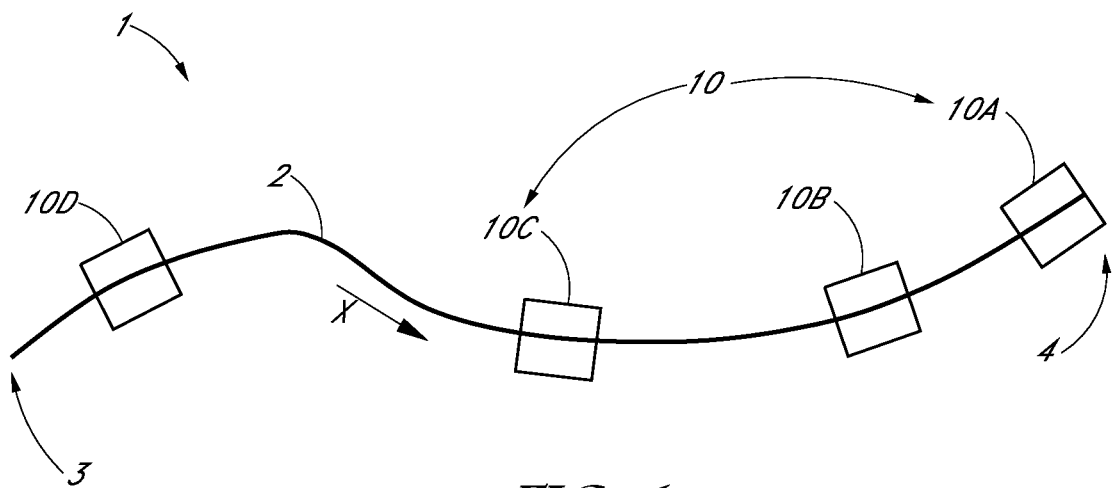
FIG. 1 is a schematic system diagram of a device comprising an elongate body and compact integrated device packages coupled to the elongate body.

Various embodiments disclosed herein relate to integrated device packages that have a compact or low profile and that may be used to sense the location of small devices. For example, various packages disclosed herein can be configured for use in devices that are inserted into a body lumen or body cavity of a human patient. In some embodiments, the integrated device packages are configured to be coupled to a guidewire that is for insertion into a body lumen or body cavity of a human patient. The embodiments disclosed herein may be particularly beneficial for use with systems that are used at a location remote from the clinician and/or access site, e.g., when the treatment or diagnosis location is not easily visible from outside the body. For example, the packages disclosed herein can be used in any suitable type of medical treatment or diagnostic procedure, including, e.g., cardiac catheter-based treatments, pill-based diagnostic and treatment techniques, endoscopy treatments, urinary catheters and endoscopes, ultrasonic imaging catheters, ear-nose-and-throat based catheters, gastroenterology treatments, colonoscopy treatments, etc. With respect to cardiac treatments, the packages disclosed herein can be used in cardiac diagnostic catheters, die delivery catheters, catheter-based pumps, optical coherence tomography (OCT) catheters, valve delivery catheters, intracardiac echocardiography (ICE) catheters, transesophageal echocardiography (TEE) catheter, diagnostic catheters, PICC lines or any other suitable device. In some embodiments, the packages disclosed herein can be coupled with the guidewire, in addition to, or as an alternative to, coupling the package to the catheter.

In various medical procedures having treatment locations remote from the clinician and/or access site, it can be important to monitor the position and/or the orientation of a working end of the medical device, e.g., the portion of the medical device that interacts with the treatment or diagnosis region. However, in many situations, it can be challenging to package sensors in a sufficiently compact profile to enable insertion into the anatomy. Similarly, in other applications compact location sensors are desirably associated with small tools or devices, particularly to aid precise positioning of such tools or devices in three dimensions.

Various embodiments herein can be utilized in conjunction with the compact device packages disclosed in U.S. patent application Ser. No. 15/681,904 ("the '904 application"), filed on Aug. 21, 2017; and in U.S. patent application Ser. No. 15/638,083 ("the '083 application"), filed on Jun. 29, 2017; the entire contents of each of which are incorporated by reference herein in their entirety and for all purposes. For example, as explained in the '904 application, in some embodiments, to package the sensors provided on the working end such that the sensors can be inserted into the anatomy, the working end can be included on an elongate bracket assembly. The elongate bracket assembly can be comprised of one or more brackets. The brackets may be separated along the longitudinal axis. Accordingly, various embodiments herein provide an elongate bracket assembly extending along a longitudinal axis of the tool or device. The elongate bracket assembly can include a first support surface and a second support surface disposed at a fixed non-parallel angle about the longitudinal axis relative to the first support surface. The fixed non-parallel angle can be about 90° in some arrangements, e.g., in a range from 89° to 91°, or in a range from 89.5° to 90.5°. A package substrate can comprise a first portion and a second portion, the first portion mechanically connected to the first support surface and the second portion mechanically connected to the second support surface. A first integrated device die can be mounted to the first portion of the package substrate. A second integrated device die can be mounted to the second portion of the package substrate. Thus, the first and second device dies can be disposed relative to one another at the fixed non-parallel angle. In some embodiments, the spatial relationship among sensors for orthogonal axes can be established without a bracket, e.g., by a molding compound.

In some arrangements, each of the first and second device dies comprises a magnetic sensor, such as an anisotropic magnetoresistance (AMR) sensor, a tunneling magnetoresistance (TMR) sensor, or a giant magnetoresistance (GMR) sensor. In various embodiments, the first die can measure the position of the package along two coordinates, and the second device die can measure the position of the package along a third coordinate. Angling the device dies relative to one another by way of deforming the package substrate can beneficially enable three-dimensional position detection of the package within the anatomy. For example, the two dies can be angled approximately perpendicular to one another to enable position sensing along three orthogonal axes. The sensor packages disclosed herein can be used in various applications, including medical devices or other technologies in which sensors are provided in small spaces. For example, in medical device implementations, the sensors can be used to sense various characteristics of the human body. Although the embodiments disclosed herein relate to position sensing, it should be appreciated that other types of sensors may be used, such as sensors that detect velocity, acceleration (e.g., accelerometers), orientation (e.g., gyroscopes), temperature, pressure, pH, etc.

FIG. 1 is a schematic system diagram of a device 1, such as a medical device, comprising an elongate body 2 having a proximal portion 3 and a distal portion 4 spaced from the proximal portion 3 along a longitudinal axis x. The longitudinal axis x may be defined in local coordinates of the elongate body 2, and may not necessarily correspond to fixed Cartesian coordinates. The elongate body 2 can comprise a medical device, such as a catheter or a guidewire. The device 1 can comprise one or a plurality of compact integrated device packages 10, such as packages 10A, 10B, 10C, 10D, coupled with the elongate body 2. The packages 10 can be disposed in a lumen of the elongate body 2 (such as an elongate catheter assembly), or can be attached to an outside surface of the elongate body 2. In some embodiments, only a single device package 10 may be coupled with the elongate body 2. In the example of a surgically or percutaneously implemented medical device, the device package 10 can be configured to provide the clinician with an indication of the position of the package 10 (and hence the portion of the elongate body 2 to which the package 10 is coupled) within the patient's anatomy. The indicated position can be provided relative to a three-dimensional coordinate system in some embodiments, so that the clinician can beneficially determine the precise location of the working end and/or a path of the elongate body 2 within the body. Thus, in some embodiments, the package(s) 10 can comprise a sensor configured to sense the position of the distal portion 4 of the body 2. In other embodiments, the package(s) 10 can comprise one or more sensors configured to transduce or sense various properties or characteristics of the anatomy. In other embodiments, however, the package(s) 10 can comprise a device that acts upon the anatomy to treat the anatomy.

In other embodiments, a plurality of device packages 10 may be disposed along a length of the elongate body 2. Utilizing a plurality of packages 10 (such as packages 10A-10D) may advantageously provide the clinician with position information of different portions of the elongate body 2. Information about the position of multiple portions of the elongate body 2 can assist the clinician in positioning the working end of the elongate body 2 relative to the anatomy. For example, in medical device applications, multiple packages 10 can be used to guide different branches of the elongate body 10 into lateral vessels (such as Y-shaped branches), and/or to position the elongate body 10 (or portions thereof) across a cardiac valve.

Figure 2:
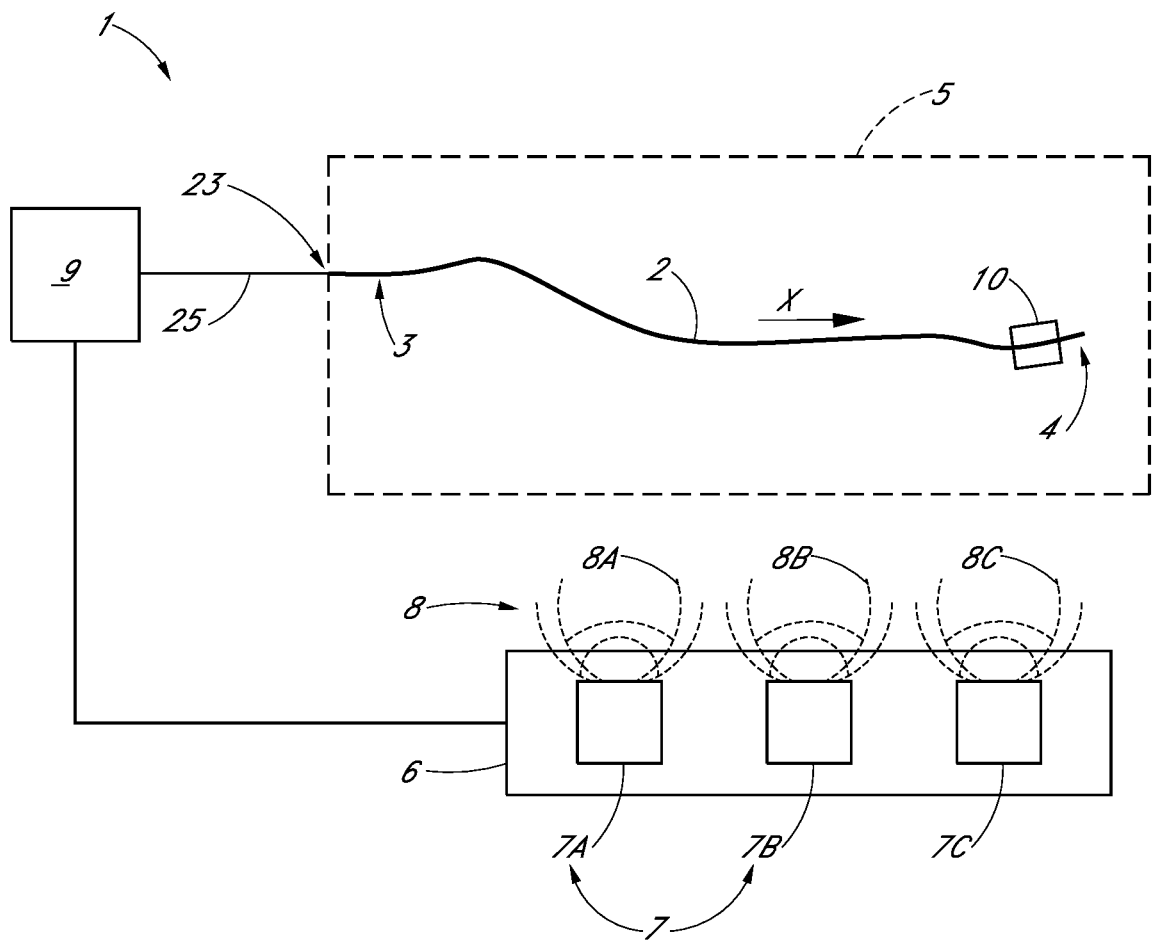
FIG. 2 is a schematic system diagram of the device of FIG. 1 during use in a procedure.

FIG. 2 is a schematic system diagram of the device 1 during use in a procedure, according to various embodiments. The device 1 can include the elongate body 2 shown in FIG. 1, with only a single integrated device package 10 coupled with the elongate body 2. It should be appreciated that multiple packages 10 can also be used in connection with FIG. 2. As shown in FIG. 2, the elongate body 2 can be disposed within an object 5 during a procedure, such as within a body of a human patient during a treatment or diagnostic procedure. During the procedure, the proximal portion 3 of the elongate body 2 can be disposed at or near an access site 23 (such as the femoral artery for cardiac catheterization procedures). One or more conduits or connectors 25 can connect the proximal portion 3 of the elongate body 2 with a console 9. The one or more conduits or connectors 25 may comprise one or more fluid conduits configured to deliver fluid to and/or remove fluid from the elongate body 2. The one or more conduits 25 may also include one or more electrical cables to provide electrical communication between the console 9 and various electrical and electronic components of the elongate body 2 (including, e.g., the package 10).

For example, the console 9 can comprise a controller that can provide power and/or ground to the device package 10 and send/receive signals by way of the one or more conduits or connectors 25 (e.g., electrical cables). The controller can comprise processing electronics configured to control the operation of the device 1. For example, the processing electronics can be programmed by way of software to implement instructions that operate the device 1. The console 9 may also include various fluid reservoirs, pumps, sensors, and other devices used in connection with the operation of the device 1. The console 9 can transmit signals to and receive signals from the package 10 at the working end of the device 1. In various embodiments, the console 9 can comprise a user interface (such as a display or touch-screen display, a keypad, etc.) that informs the clinician about the status of the procedure and/or the location of the working end of the device 1. The clinician can input instructions to the console 9 by way of the user interface to select various settings and/or operational modes of the device 1 during and/or before use. In some embodiments, the console 9 can be connected to an external processing device (e.g., a computer) that can, for example, act as the user interface and/or analyze operation data. In some embodiments, the console 9 can receive the signals from the package 10, and can provide feedback to the package 10 with further instructions based on the received signals.

In some embodiments, as explained herein and in the '904 application, the package 10 can comprise a position sensor package configured to determine an approximate position of the package 10, and therefore the portion of the elongate body 2 to which the package is connected. In some embodiments, for example, the package 10 can comprise a magnetic sensor package, and particularly a magnetoresistance sensor package, e.g., an anisotropic magnetoresistance (AMR) sensor package, a tunneling magnetoresistance (TMR) package, or a giant magnetoresistance (GMR) package. For example, AMR packages, such as the packages 10 disclosed herein and in the '904 application, can comprise a plurality of AMR sensor dies having an anisotropic material in which electrical resistance depends on an angle between the direction of electrical current and the direction of the magnetic fields sensed by the anisotropic material. In some arrangements, for example, the resistance may be maximized when the direction of current is parallel to the magnetic field, and the resistance may be reduced at other angles.

As shown in FIG. 2, a transmitter 6 that includes a magnetic generator 7 may be provided with the device 1 so as to generate a magnetic field 8 to be transduced by the package 10. The magnetic generator 7 may comprise one or a plurality of magnetic generators, each of which may comprise one or a plurality of coiled wires. In the illustrated embodiment, for example, the magnetic generator 7 comprises a plurality of magnetic generators 7A, 7B, 7C spaced from one another by predetermined spacings. Each magnetic generator 7A-7C of the plurality of magnetic generators can be configured to generate a respective magnetic field 8A-8C at different frequencies. In some arrangements, the console 9 can control the operation of the magnetic generator 7, while in other embodiments, the magnetic generator 7 may be controlled separately from the console 9 to which the elongate body 2 is connected. The generated magnetic fields 8A-8C may be sufficiently strong so as to penetrate the object 5 and to be sensed by the package 10. For example, in some embodiments, the object 5 (e.g., human patient) may lie on a table, with the magnetic generators 7A-7C disposed under the table and object 5.

In various embodiments, the package 10 can be configured to detect the generated magnetic fields 8A-8C. The integrated device package 10 can be configured to transmit signals to the controller of the console 9 that are indicative of a position of the integrated device package 10. The package 10 can comprise one or a plurality of integrated device dies that can detect the components of the magnetic fields 8A-8C in, for example, three dimensions. The signals can be transmitted to the controller by way of the conduit(s) or connector(s) 25. The controller can include processing electronics configured to analyze the signal to determine the position of the integrated device package 10. For example, the controller can be configured to compare the signals transmitted by the package 10 with the data about the fields 8A-8C generated by the magnetic generators 7A-7C, and/or to compare the signals transmitted from each die of the package 10 with one another. In some embodiments, the magnetic fields 8A-8C may comprise different frequencies that are detectable by the processing electronics. The controller can therefore associate each of the fields 8A-8C detected by the package 10 with an associated magnetic generator 7A-7C, based at least in part on the associated frequency of the fields 8A-8C. The known positions of the magnetic generators 7A-7C in a global set of Cartesian coordinates (e.g., X, Y, Z) set by the console 9 can be used to triangulate the position, rotation, and/or orientation of the package 10 in and about three dimensions. The processing electronics of the controller can therefore be configured to determine the position of the integrated device package 10 based on a comparison of the respective position signals of each sensor die in the package 10. In some arrangements, the differential output signals from the dies may comprise a pair of twisted wires or a pair of wires spaced closely to one another. Such an arrangement may beneficially reduce any inductance from the magnetic generator 7 in the differential output signal.

Although the integrated device package 10 disclosed in FIG. 2 comprises a position sensor package, the package 10 can comprise any suitable type of package. For example, in various embodiments, the package 10 can comprise other types of sensor(s) configured to sense or detect properties or characteristics of the anatomy. In other embodiments, the package 10 can comprises electrical and/or mechanical components that are configured to act upon or treat the anatomy.

As explained herein, the electronic devices (e.g., integrated device packages, sensor modules, etc.) may be provided within a body cavity of a patient to sense various parameters associated with the electronic device and/or the patient's anatomy. In such procedures, the integrated device package 10 may be provided at a location remote from the location at which the medical device enters the patient (such as an insertion site for a percutaneous insertion procedure). For example, in some embodiments, the integrated device package 10 can be inserted through a catheter assembly to a treatment region of the patient (e.g., the heart for some cardiac procedures) that is remote from the location at which the catheter assembly is introduced (e.g., the femoral artery, or other vascular access site remote from the heart). The integrated device package 10 can sense or otherwise act upon the treatment region at the remote location. Due at least in part to the remote operation of the system and to the small spaces associated with the operating environment (e.g., the vascular system), it can be challenging to provide electronic communication between the package and the system controller which controls the operation of the system. Wireless communications may be impractical due to the limited space within the lumen for complex communications chips or circuits, in addition to concerns about reliability of such communications and interference with other electronics.

Thus, various embodiments herein utilize an elongate electrical connector to provide electrical communication between a proximal portion of the system and a distal portion of the system to which the integrated device package (e.g., sensor module) is coupled. During use of the system, the distal portion (with the device package) can be provided at the treatment region at a location remote from the proximal portion. The proximal portion of the system can mechanically and/or electrically connect to a system controller, such as the console 9, by way of the elongate electrical connector. During operation of the system, therefore, the electrical connector can extend from the distal portion (and the package) to a location outside the body of the patient (e.g., to the console 9 illustrated in FIG. 2). However, it can be challenging to provide an electrical connector that is sufficiently long to connect to the package at the remote treatment site, that is sufficiently narrow and flexible for operation within small lumens such as for a catheter assembly that is to be guided through a body cavity, and that provides electrical communication over multiple channels to monitor and control the operation of the system.

Referring to FIGS. 3A-4C, in some embodiments, an integrated device package 10 (e.g., sensor module) can connect to a console (not shown) by way of an elongate electrical connector 11 that comprises an elongate flexible substrate 12. As shown in FIGS. 3A-4C, the elongate flexible substrate 12 has a proximal portion 13 and a distal portion 14 spaced from the proximal portion 13 by a length l1 along a longitudinal axis. The longitudinal axis may be defined in local coordinates of the elongate flexible substrate 12, and may not necessarily correspond to fixed Cartesian coordinates. The elongate flexible substrate 12 can have a width w1 along an axis transverse to the longitudinal axis, with the elongate flexible substrate 12 defining an elongation ratio of the length l1 to the width w1. In some embodiments, the elongation ratio can be at least 100:1. In some embodiments, the elongation ratio can be at least 500:1, at least 1000:1, at least 2000:1, at least 4000:1, or at least 10,000:1. In some embodiments, the elongation ratio can be in a range of 250:1 to 15,000, in a range of 250:1 to 12,500, in a range of 500:1 to 12,500:1, in a range of 250:1 to 8,000:1, in a range of 250:1 to 4000:1, in a range of 250:1 to 2000:1, in a range of 250:1 to 1000:1, in a range of 250:1 to 500:1, or in a range of 500:1 to 1000:1. The integrated device package 10 (e.g., sensor module) can be mechanically and electrically connected to the distal portion 14 of the elongate flexible substrate 12 by way of a connection portion 16. In some embodiments, the connecting portion 16 can also comprise a flexible substrate, e.g., an insulating substrate with embedded conductive traces and contacts.

In various embodiments, the elongate flexible substrate 12 can comprise one or a plurality of conductive layers at least partially embedded in an insulating material (e.g., polyimide, or an inorganic dielectric). In some embodiments (e.g., FIGS. 3A-3C), the elongate flexible substrate 12 can comprise a single conductive (e.g., metal) layer ML1, which is shown schematically in phantom in FIG. 3C. In other embodiments (e.g., FIGS. 4A-4C), the elongate flexible substrate 12 can comprise multiple (e.g., two) conductive (e.g., metal) layers, ML1 and ML2, shown as schematic layers in phantom in FIG. 4C. In some embodiments, the elongate flexible substrate 12 with multiple conductive layers may be thicker than the elongate flexible substrate 12 with a single conductive layer. The illustrated embodiments of FIGS. 3A-3C only employ seven conductive lines to power and receive sensed data from the sensor package 10, and can readily be wired in a single metal layer and still provide a sufficiently narrow flexible substrate to provide flexibility within a catheter lumen. However, providing two metal layers within the flexible substrate 12, as in FIGS. 4A-4C, allows routing a single line through both metal layers by using, for example, elongate extensions, periodic jogs across the width dimension and vertical vias. Such routing can enable a helical arrangement of the conductive lines along the length l1 of the flexible substrate 12. Thus, for example, two lines can be intertwined as a closely spaced, twisted pair along the length of the flexible substrate 12. Such an arrangement may beneficially reduce any inductance from, for example, the magnetic generator 7 shown in FIG. 2 in the differential output signal.

In some embodiments, the elongate flexible substrate 12 can comprise a flexible insulating material (e.g., a polymer, such as polyimide, or an inorganic dielectric) with embedded conductors (e.g., traces and contacts) configured to provide electrical communication to and/or from the integrated device package. The conductors can comprise conductive lines extending along the length l1 of the flexible substrate 12. In some embodiments, each conductive line can be spaced from one another along the width w1 of the flexible substrate 12. A skilled artisan will understand that the flexible substrate 12 can have any suitable number of conductive lines.

The integrated device package 10 can be any suitable type of device package, including a sensor, an actuator, etc. The package 10 can include any suitable number or type of electronic components, including processor dies, microelectromechanical systems (MEMS) dies, motion sensor dies, optical dies, etc. The dies and other components (not illustrated) can be embedded in a molding compound 33, as shown in FIGS. 3A-4C. The molding compound 33 can serve to protect and/or mechanically fix the integrated device dies, in some embodiments. In the illustrated embodiments, for example, the integrated device package 10 can comprise a sensor module, e.g., a position sensor such as an anisotropic magnetoresistance (AMR) sensor. As illustrated in FIGS. 3A-4C, the integrated device package 10 can comprise a connection portion 16 that can be connected to the distal portion 14 of the elongate flexible substrate 12. In some embodiments the connection portion 16 can comprise a flexible substrate with conductive material embedded therein.

Figure 3C:
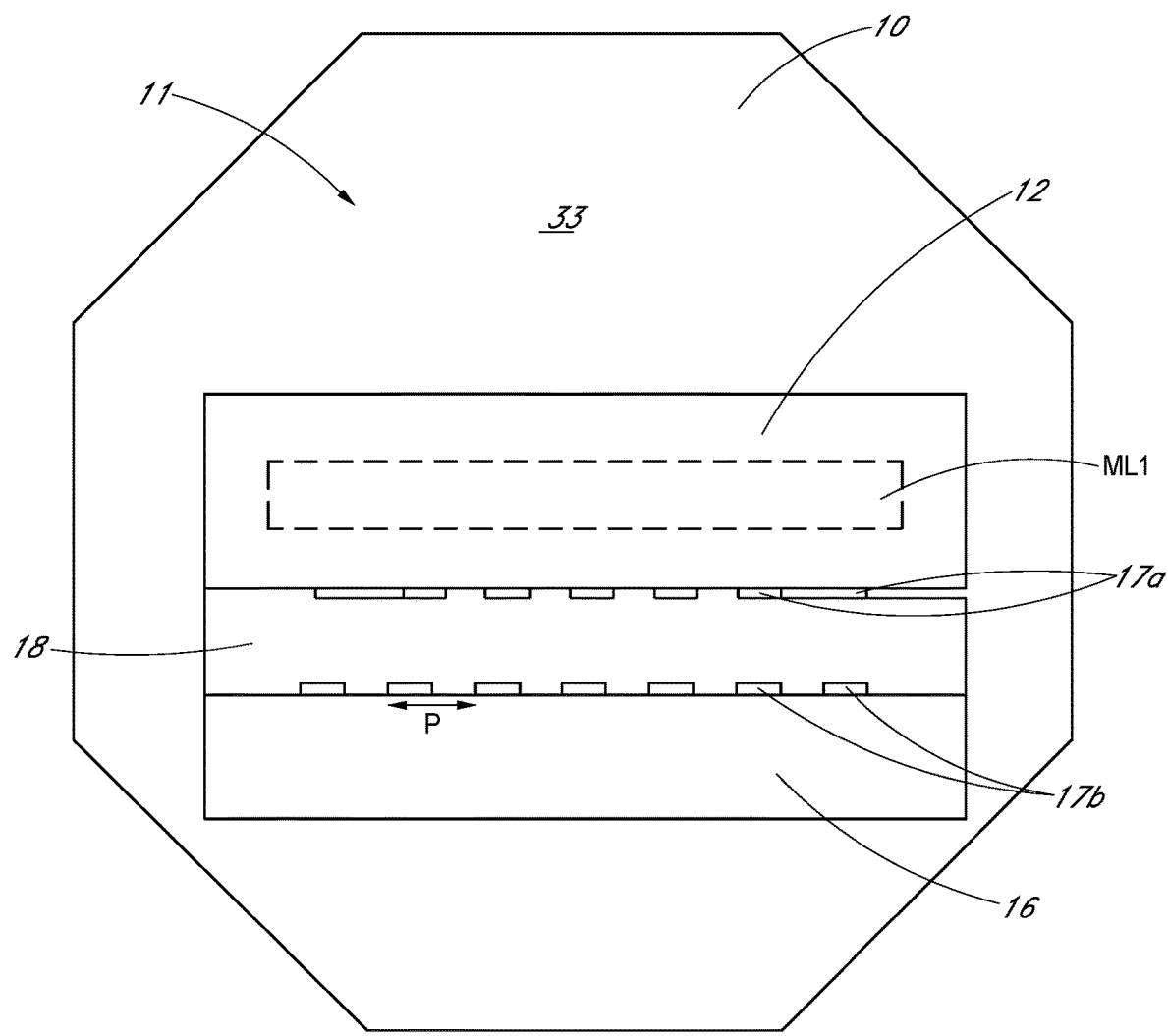
FIG. 3C is an end view of the integrated device package and the elongate electrical connector of FIG. 3A.
Figure 4C:
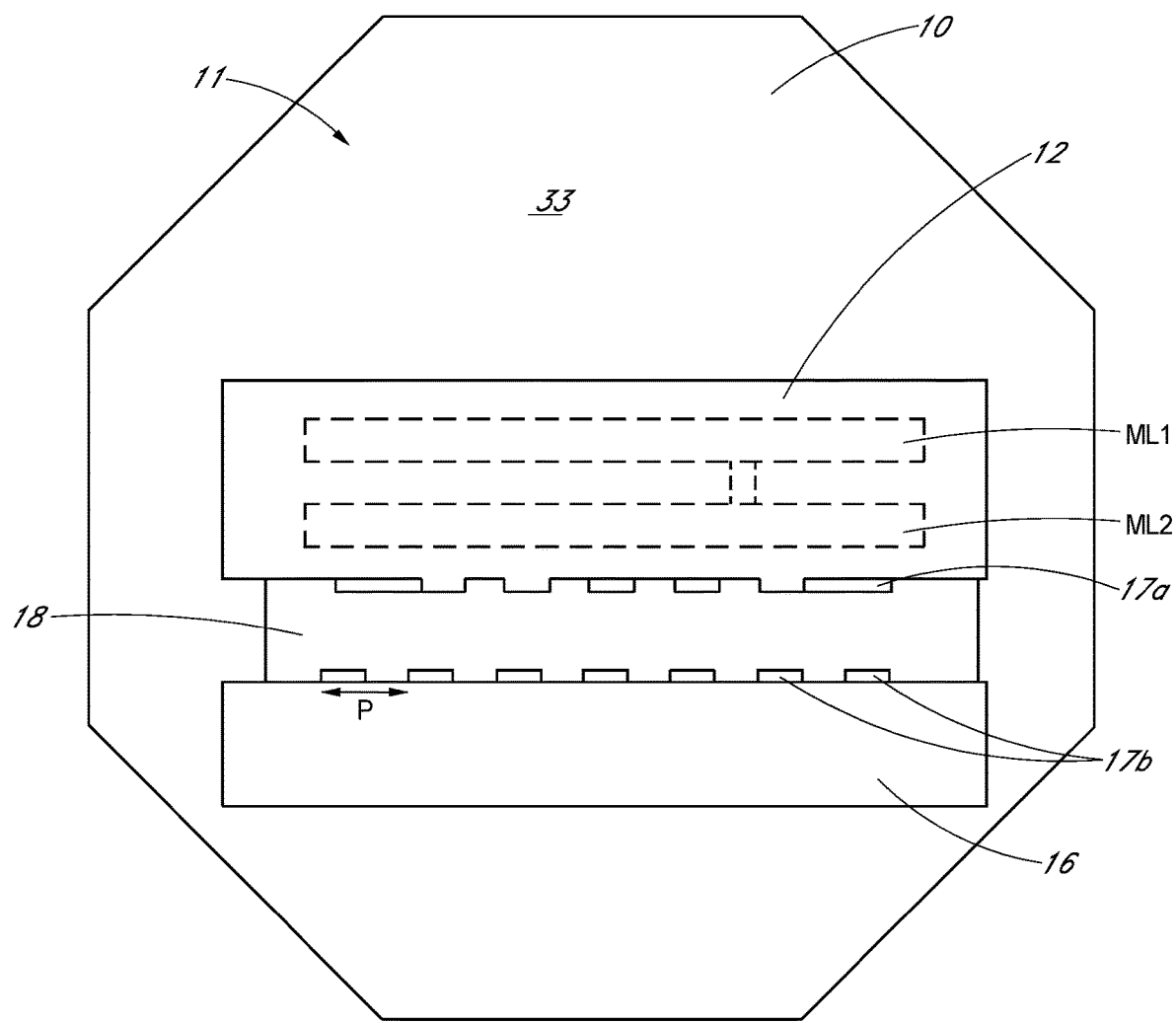
FIG. 4C is an end view of the integrated device package and the elongate electrical connector of FIG. 4A.

In various embodiments, the length l1 of the elongate flexible substrate 12 can be in a range of 0.5 m to 2.5 m, for example, in a range of 1 m to 2 m. The width w1 of the elongate flexible substrate 12 can be in a range of 0.2 mm to 0.5 mm, or in a range of 0.25 mm to 0.45 mm. As illustrated in FIGS. 3C and 4C, the distal portion 14 of the elongate flexible substrate 12 can be bonded to the connection portion 16 of the integrated device package 10 by an adhesive 18. In various embodiments, the adhesive 18 can comprise anisotropic conductive film (ACF) or anisotropic conductive paste (ACP). Further, the elongate flexible substrate 12 can comprise a plurality of electrical contacts 17a spaced laterally by a pitch, the pitch being in a range of 30 microns to 50 microns. Similarly, the connection portion 16 can comprise a plurality of electrical contacts 17b spaced apart by a pitch, which may be the same as or different from the pitch of the contacts 17a. Advantageously, ACF or ACP can mechanically connect the flexible substrate 12 to the integrated device package 10 (e.g., the sensor module) as well as electrically connect multiple pads for signal, power and/or ground. In some embodiments, the elongate flexible substrate 12 can comprise at least two metal layers spaced apart by an insulating material. The elongate flexible substrate 12 can comprise a pair of metallic lines defined in the at least two metal layers and a plurality of vias extending between the at least two metal layers, each metallic line of the pair of metallic lines traversing a helical pathway along the at least two metal layers and the plurality of vias.

In various embodiments, an electronic device that comprises the integrated device package 10 and the elongate electrical connector 11 can be used in conjunction with a medical device and/or procedure. In such embodiments, the electronic device (e.g., the device 1 shown in FIGS. 1 and 2) can be disposed along and/or within an elongate catheter assembly. As explained herein, the electronic device can be guided within the elongate catheter assembly to a treatment location. The electronic device can be used to sense various parameters associated with the electronic device and/or the patient's anatomy. In other embodiments, the electronic device can act upon or otherwise treat the anatomy.

Figure 5A:
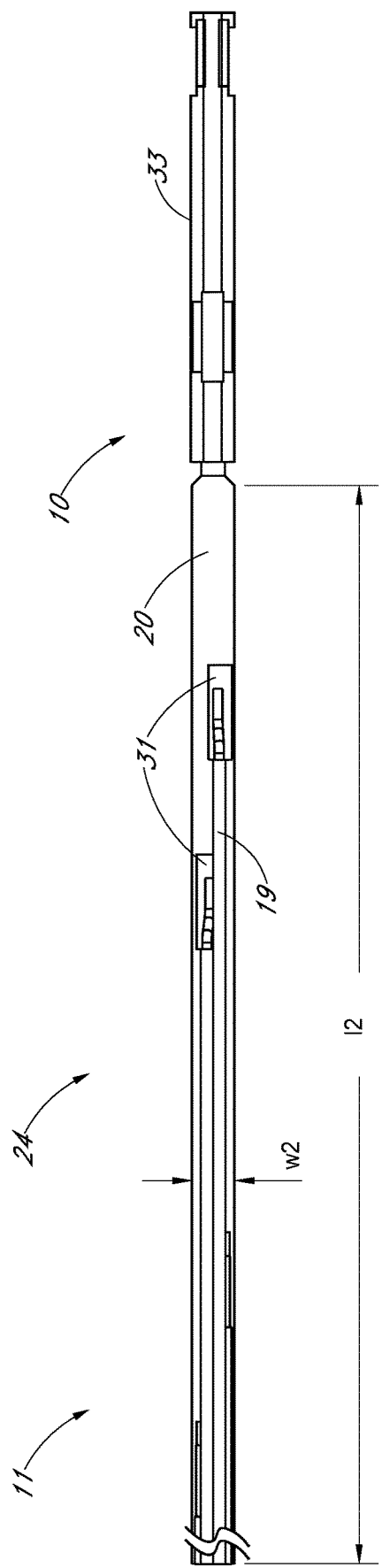
FIG. 5A is a schematic top view of an integrated device package connected to an elongate electrical connector that comprises wiring cables.
Figure 6A:
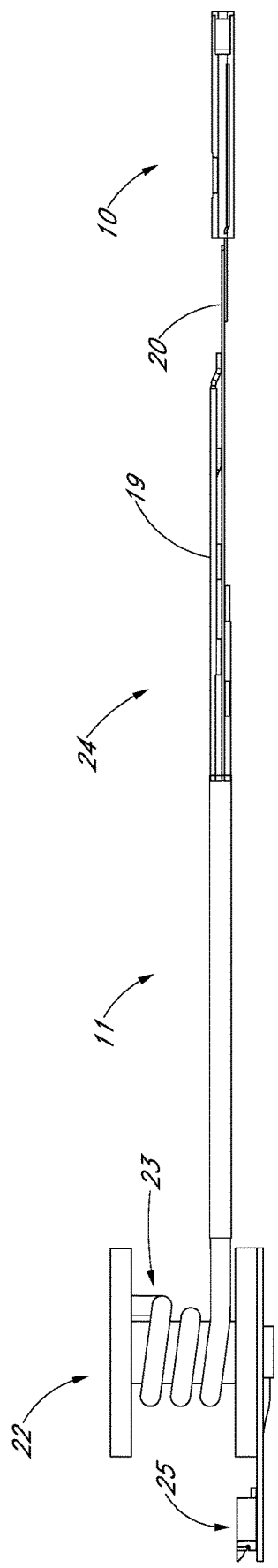
FIG. 6A is a schematic side view of an elongate electrical connector that is connected to a bobbin attached to a system board interface at a proximal portion of the elongate electrical connector and to an integrated device package at a distal portion of the elongate electrical connector.

FIGS. 5A and 5B illustrate the integrated device package 10 (e.g., sensor module) connected to an elongate electrical connector 11 that comprises a cable 19 (e.g., wiring cables 19a-19g shown in FIG. 5C). The elongate connector may also include a substrate 20 (e.g., a flexible substrate). In such embodiments the wiring cables 19a-19g can be connected to the substrate 20, for example, by way of a plurality of conductive lands 31 (for example, with solder balls or other conductive adhesive). However, in some embodiments the integrated device package 10 can comprise the substrate 20 to which the wiring cables 19a-19g may connect. The elongate electrical connector 11 has a proximal portion 23 (see, for example, FIGS. 6A and 7A) and a distal portion 24 spaced from the proximal portion 23 by a length l2 along a longitudinal axis. The longitudinal axis may be defined in local coordinates of the elongate electrical connector 11, and may not necessarily correspond to fixed Cartesian coordinates. The elongate electrical connector 11 can have a width w2 along an axis transverse to the longitudinal axis, with the elongate electrical connector 11 defining an elongation ratio of the length l2 to the width w2, which may be the same as or different from the elongation ration of the length l1 to the width w1 described above. In some embodiments, the elongation ratio can be at least 100:1. In some embodiments, the elongation ratio can be at least 500:1, at least 1000:1, at least 2000:1, at least 4000:1, or at least 10,000:1. In some embodiments, the elongation ratio can be in a range of 250:1 to 15,000, in a range of 250:1 to 12,500, in a range of 500:1 to 12,500:1, in a range of 250:1 to 8,000:1, in a range of 250:1 to 4000:1, in a range of 250:1 to 2000:1, in a range of 250:1 to 1000:1, in a range of 250:1 to 500:1, or in a range of 500:1 to 1000:1. The integrated device package 10 (e.g., sensor module) can be mechanically and electrically connected to the distal portion 14 of the elongate electrical connector 11. In various embodiments, the length l2 of the elongate electrical connector 11 can be in a range of 0.5 m to 2.5 m, or in a range of 1 m to 2 m. The width w2 of the elongate electrical connector 11 can be in a range of 0.2 mm to 1 mm.

As illustrated in FIG. 5C, the elongate electrical connector 11 can comprise seven cables 19a-19g arranged to fit in a certain dimension. For example, as illustrated in FIG. 5C, five cables 19a-19e are disposed on one side of the substrate 20, and two cables are disposed on the other side of the substrate 20. The cable 19a-19g can have a diameter d. In some embodiments, the diameter d can of the cable 19a-19g can be in a range of 100 μm to 150 μm. In some embodiments, the cable 19a-19g can comprise an insulating layer around the cable 19a-19g. The insulating material may have a thickness in a range of 5 μm to 30 μm, in some embodiments. At the distal portion 24 of the elongate electrical connector 11, the cables 19a-19g can be connected to the substrate 20 by way of the lands 31 and a suitable conductive adhesive (e.g., solder). In some embodiments, the cables 19a-19g can be connected to the substrate 20 at different longitudinal locations, as shown in FIGS. 5A and 5B. The substrate 20 can be electrically and mechanically connected with the integrated device package 10. The cables 19a-19e and substrate 20 can be sized sufficiently small so as to fit within a catheter that is guided within the body of a patient. In various embodiments, the cables 19a-19e and substrate 20 can be packaged to fit within a major dimension or diameter of less than 0.75 mm, less than 0.6 mm, or less than 0.5 mm. In various embodiments, the cables 19a-19e and substrate can be packaged to fit within a major dimension or diameter in a range of 0.3 mm to 0.75 mm, or in a range of 0.35 mm to 0.65 mm, or in a range of 0.35 mm to 0.55 mm.

FIGS. 6A-7C show the elongate electrical connector 11 that is connected to the integrated device 10 and a bobbin 22. Therefore, in some embodiments, the integrated device package 10 can electrically connect with the console 9 (see, for example, FIG. 2) or other controller by way of an elongate electrical connector 11 that can be initially spooled on a rotatable bobbin 22. Beneficially, the rotatable bobbin 22 can enable the clinician to unspool a desired length of the elongate connector 11 so as to guide the package 10 to the target location or treatment site. Thus, the embodiments disclosed herein can enable the use of the electronic device in conjunction with treatment locations that may be located at variable lengths within the patient. The connector 11 can comprise a plurality of wires 19 disposed within a shield or cover as explained above. In other embodiments, the connector can comprise an elongate substrate, such as that shown in FIGS. 3A-4C.

For example, in some embodiments (see FIGS. 5A-7C), an electronic device can comprise a bobbin 22 and an elongate electrical connector 11 configured to unspool from the bobbin 22. The elongate electrical connector 11 can have the proximal portion 23 that mechanically couples to the bobbin and the distal portion 24 that is configured to connect to the integrated device package 10. The integrated device package 10 (e.g., a sensor module) can be mechanically and electrically coupled with the distal portion 24 of the elongate electrical connector 11 as explained above.

In the illustrated embodiments of FIGS. 5A-7C, the elongate electrical connector 11 can comprise a plurality of cables 19a-19g. As shown the cables 19a-19g can be shielded with a shielding material 21 so as to protect the anatomy of the patient. In various embodiments, a major lateral dimension of the elongate electrical connector 11 can beneficially be in a range of 0.3 mm to 1 mm, such that the connector can be inserted into relatively narrow body cavities of the patient.

Figure 6B:
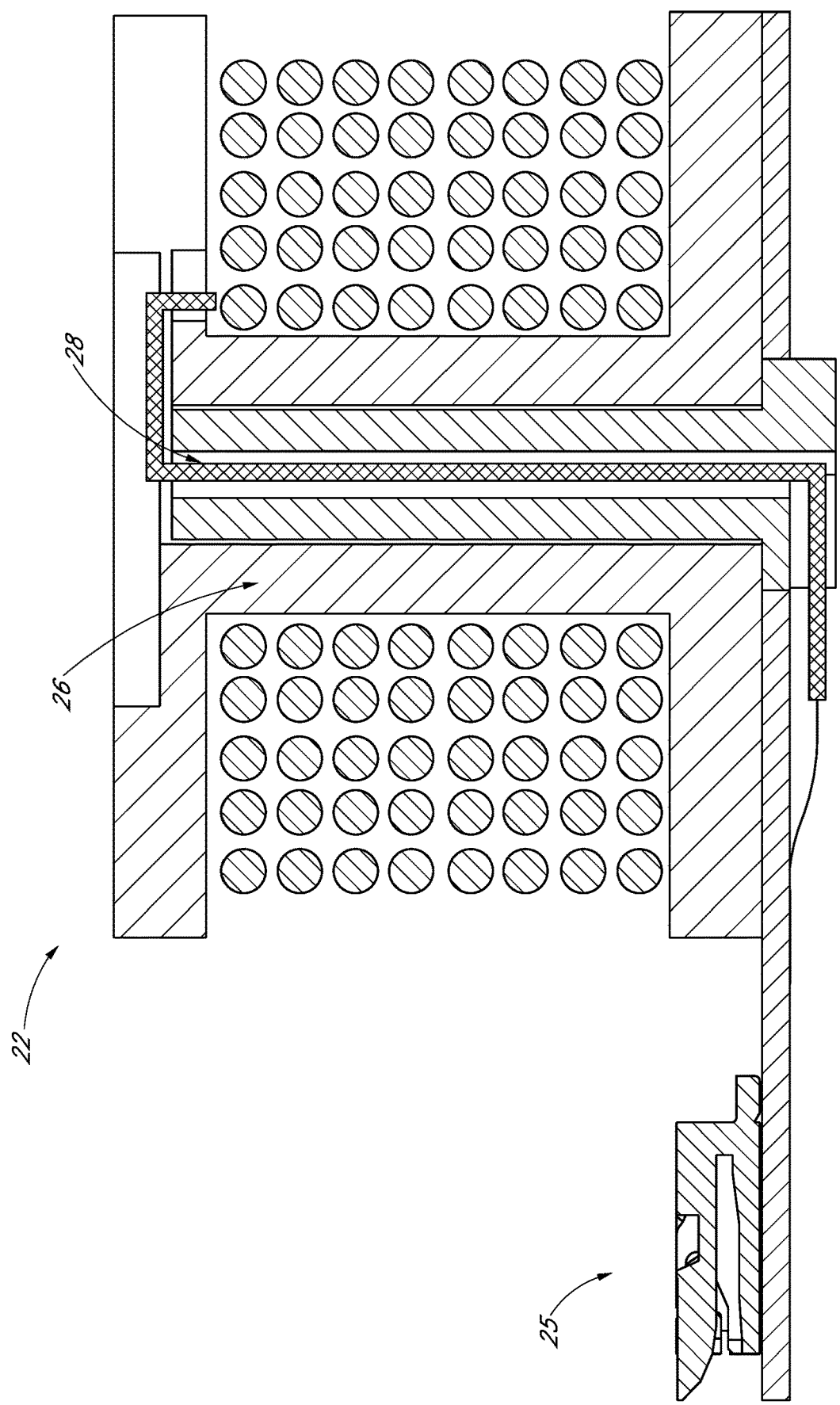
FIG. 6B is a cross sectional view of the bobbin of FIG. 6A with the elongate electrical connector wound around the bobbin.
Figure 6C:
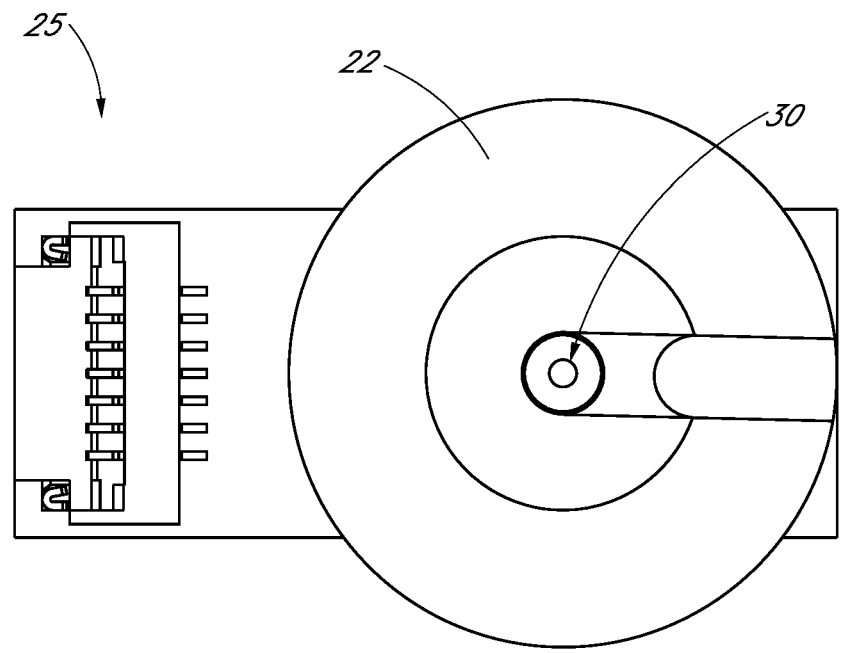
FIG. 6C is a schematic top view of the bobbin and the system board interface of FIG. 6B.
Figure 6D:
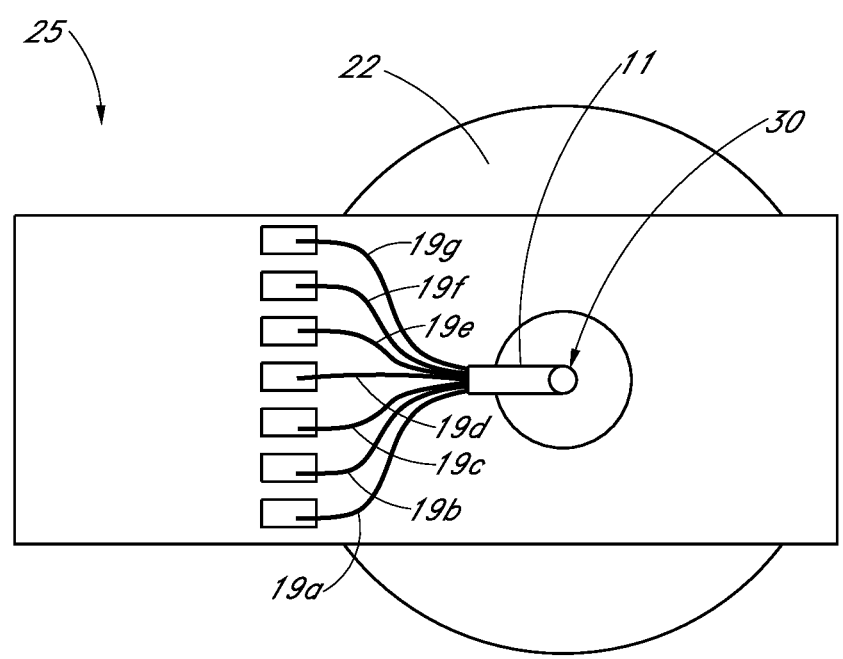
FIG. 6D is a schematic bottom view of the bobbin and the system board interface of FIG. 6B.

As shown in FIGS. 6B-6D and 7B-7C, the proximal portion 23 of the elongate electrical connector 11 can be configured to connect to a system board (not shown, such as a printed circuit board, or PCB). The system board can be located in or otherwise electrically connected with the overall system controller, e.g., the console 9 illustrated in FIG. 2. The controller or console can interface the system board to control the operation of the integrated device package 10. As shown in FIGS. 6B-6D, in some embodiments, the bobbin 22 can be fixed to a system board interface 25 (e.g., flex-circuit connector, etc.), which in turn is configured to be connected to the system board (not shown). The bobbin 22 can rotate relative to the system board interface 25 (e.g., by way of a pin) to unspool the electrical connector. In such embodiments, as shown in FIG. 6B, the bobbin 22 can comprise a spool 26 with a channel 28 along the axis of rotation, and the proximal portion 23 of the elongate electrical connectors 11, or wires, can extend through the channel 28 in the spool 26 to extend to the system board interface 25. When mounted on the system board, the bobbin 22 can spool or unspool the connectors 11 as needed. In some embodiments, the bobbin 22 can comprise a pin hole 30 configured to receive a pin disposed on the system board.

Figure 7A:
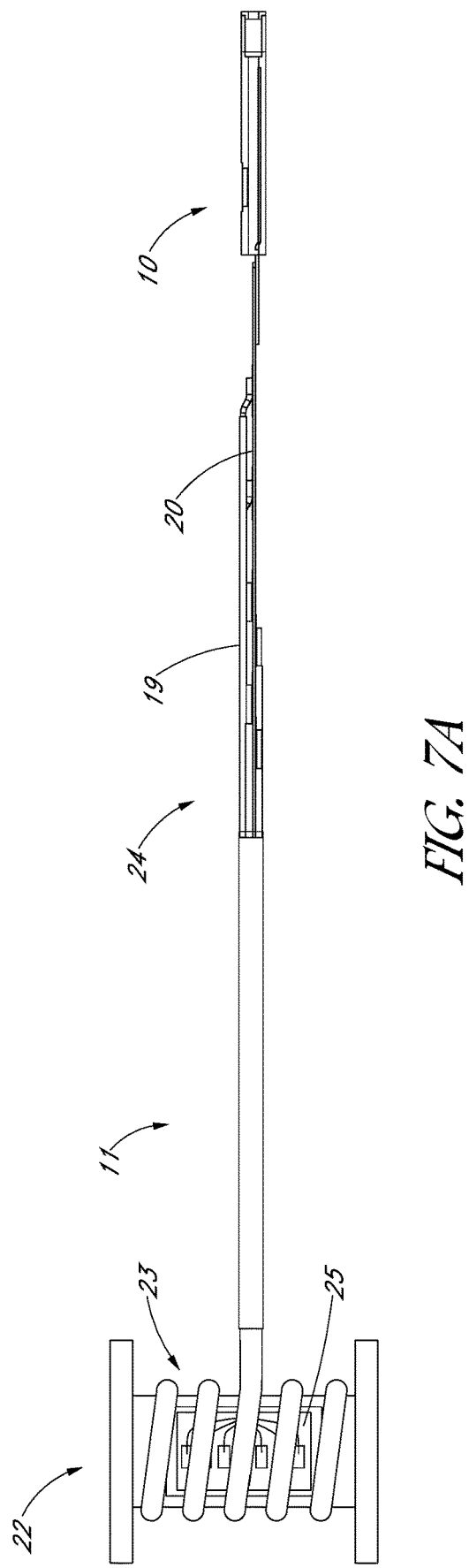
FIG. 7A is a schematic side view of an elongate electrical connector with a system board interface that is coupled to a bobbin at a proximal portion of the elongate electrical connector and to an integrated device package at a distal portion of the elongate electrical connector.
Figure 7C:
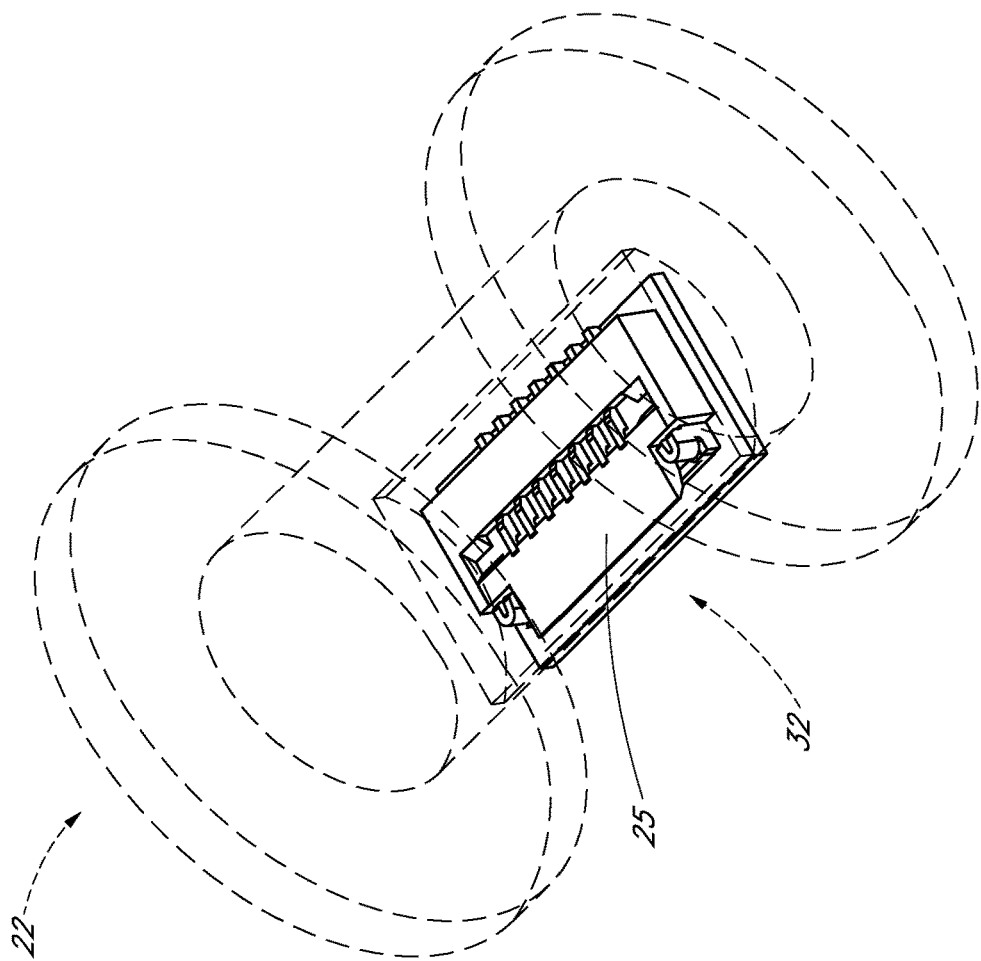
FIG. 7C shows the system board coupled with the bobbin.
Figure 7B:
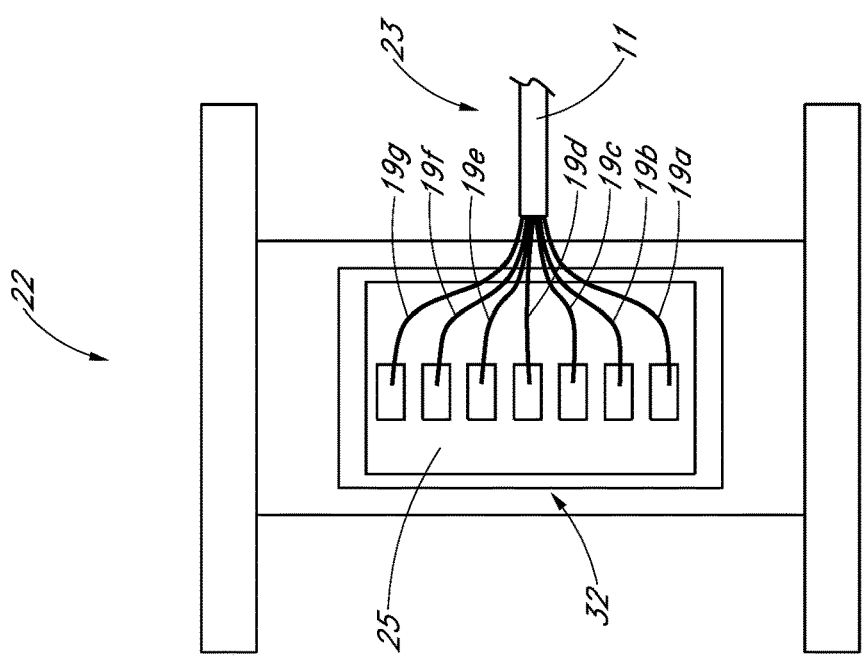
FIG. 7B is a schematic side view of the bobbin and the elongate electrical connector of FIG. 7A.

In other embodiments, such as the embodiment shown in FIGS. 7A-7C, a system board interface 25 can be connected to the proximal portion 23 of the elongate electrical connector 11, with the board interface 25 coupled to or disposed in a portion (e.g., an interface holder 32) of the bobbin 22, such as a pocket or cavity of the bobbin 22. In such embodiments, after unspooling the connector, the system board interface 25 may be removable from the bobbin 22. Once removed, the clinician can connect the system board interface 25 to the system board of the console or controller in any suitable manner. In FIGS. 7A-7C, the interface holder 32 is located near the middle of the bobbin 22 such that the elongate electrical connector 11 winds around the interface 25. However, the interface holder 32 may be located at any portion of the bobbin 22.

As discussed above the elongate electrical connector 11 can be connected to the integrated device package 10. In various embodiments, the distal portion 24 of the elongate electrical connector 11 can include a plurality of connectors that connect to a proximal connector of the integrated device package 10. The plurality of connectors can connect to the proximal connector at a plurality of staggered locations along the proximal connector of the integrated device package 10. As explained herein, in some embodiments, the integrated device package 10 can comprise a sensor module, such as a position sensor (e.g., an anisotropic magnetoresistance (AMR) sensor). In various arrangements, a length of the elongate electrical connector 10 can be in a range of 0.5 m to 2.5 m.

Although FIGS. 6A-7C illustrate embodiments that include the elongate electrical connector 11 of FIGS. 5A-5C (e.g., the elongate electrical connector 11 that comprises wiring cable 19a-19g within a cover or shield member), the embodiments may include the elongate electrical connector 11 of FIGS. 3A-4C (e.g., the elongate electrical connector 11 that comprises elongate flexible substrate 12). For example, the elongate flexible substrate 12 can be wound around the bobbin 22.

As explained above, the electronic devices disclosed herein can be used in conjunction with various types of medical treatment procedures. In some embodiments, a method of operating an electronic device that includes an integrated device package coupled with a distal portion of an elongate electrical connector is disclosed. The method can include unspooling the elongate electrical connector from a bobbin, with a proximal portion of the elongate electrical connector being coupled with the bobbin (e.g., configured to be spooled about). The integrated device package can be guided to a target location in a body cavity of a patient.

In various embodiments, for example, a catheter assembly can be inserted into the body cavity. The integrated device package and at least a portion of the elongate electrical connector can be provided within a lumen of the catheter assembly. In some embodiments, the method can include determining a position of the integrated device package within the body cavity of the patient. In some embodiments (e.g., FIGS. 6A-6D), the bobbin can be attached to a system board interface and the proximal portion of the elongate electrical connector can be electrically connected to corresponding pads on the system board interface. In some embodiments (e.g., FIGS. 7A-7C), a system board interface can be removed from the bobbin (e.g., from a pocket or cavity of the bobbin), with the system board interface being electrically connected to the proximal portion of the elongate electrical connector.

Although disclosed in the context of certain embodiments and examples, it will be understood by those skilled in the art that the present invention extends beyond the specifically disclosed embodiments to other alternative embodiments and/or uses and obvious modifications and equivalents thereof. Further, unless otherwise noted, the components of an illustration may be the same as or generally similar to like-numbered components of one or more different illustrations. In addition, while several variations have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the present disclosure. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the aspects that follow.

What is claimed is:

1. An electronic device comprising:
   an elongate flexible substrate having a proximal portion and a distal portion spaced from the proximal portion by a length along a longitudinal axis, the elongate flexible substrate having a width along an axis transverse to the longitudinal axis, the elongate flexible substrate defining an elongation ratio of the length to the width, the elongation ratio being at least 100:1; and
   an integrated device package mechanically and electrically connected to the distal portion of the elongate flexible substrate,
   wherein the elongate flexible substrate comprises a flexible insulating material with embedded conductors configured to provide electrical communication to and/or from the integrated device package.

2. The electronic device of claim 1, wherein the integrated device comprises a second flexible substrate, the portion of the second flexible substrate being mechanically and electrically connected to the distal portion of the elongate flexible substrate.

3. The electronic device of claim 1, wherein the integrated device package comprises a position sensor.

4. The electronic device of claim 3, wherein the sensor module comprises an anisotropic magnetoresistance (AMR) sensor.

5. The electronic device of claim 1, wherein the length of the elongate flexible substrate is in a range of 0.5 m to 2.5 m, and the width of the elongate flexible substrate is in a range of 0.2 mm to 0.5 mm.

6. The electronic device of claim 1, wherein the distal portion of the elongate flexible substrate is bonded to a portion of the integrated device package by an adhesive, wherein the adhesive comprises anisotropic conductive film or anisotropic conductive paste.

7. The electronic device of claim 1, wherein the elongate flexible substrate comprises a plurality of electrical contacts spaced laterally by a pitch, the pitch being in a range of 30 microns to 50 microns.

8. The electronic device of claim 1, wherein the elongate flexible substrate comprises at least two metal layers spaced apart by an insulating material, wherein the elongate flexible substrate comprises a pair of metallic lines defined in the at least two metal layers and a plurality of vias extending between the at least two metal layers, each metallic line of the pair of metallic lines traversing a helical pathway along the at least two metal layers and the plurality of vias.

9. An electronic device comprising:
   a bobbin;
   an elongate electrical connector configured to unspool from the bobbin, the elongate electrical connector having a distal portion and a proximal portion that mechanically couples to the bobbin; and
   an integrated device package coupled with the distal portion of the elongate electrical connector,
   wherein the elongate electrical connector comprises a flexible insulating material with embedded conductors configured to provide electrical communication to and/or from the integrated device package.

10. The electronic device of claim 9, wherein a major lateral dimension of the elongate electrical connector is in a range of 0.3 mm to 1 mm.

11. The electronic device of claim 9, wherein the proximal portion of the elongate electrical connector is connected to a system board interface configured to connect to a system board, wherein a length of the elongate electrical connector is in a range of 0.5 m to 2.5 m.

12. The electronic device of claim 11, further comprising the system board interface connected to the proximal portion of the elongate electrical connector, the system board interface coupled to or disposed in a portion of the bobbin, wherein the system board interface is removable from the bobbin.

13. The electronic device of claim 9, wherein the bobbin is configured to rotate about a spool, the proximal portion of the elongate electrical connector extending through a channel in the spool.

14. The electronic device of claim 9, wherein the distal portion of the elongate electrical connector comprises a plurality of connectors that connect to a proximal connector of the integrated device package, wherein the plurality of connector connect to the proximal connector at a plurality of staggered locations along the proximal connector.

15. The electronic device of claim 9, wherein the integrated device package comprises a position sensor.

16. A method of operating an electronic device that includes an integrated device package coupled with a distal portion of an elongate electrical connector, the method comprising:
   unspooling the elongate electrical connector from a bobbin, a proximal portion of the elongate electrical connector being coupled with the bobbin, the elongate electrical connector comprising a flexible insulating material with embedded conductors configured to provide electrical communication to and/or from the integrated device package; and
   guiding the integrated device package to a target location in a body cavity of a patient.

17. The method of claim 16, further comprising inserting a catheter assembly into the body cavity, and providing the integrated device package and at least a portion of the elongate electrical connector within a lumen of the catheter assembly.

18. The method of claim 16, further comprising determining a position of the integrated device package within the body cavity of the patient.

19. The method of any one of claim 16, further comprising attaching the bobbin to a system board interface and electrically connecting the proximal portion of the elongate electrical connector to corresponding pads on the system board interface.

20. The method of claim 16, further comprising removing a system board interface from the bobbin, the system board interface electrically connected to the proximal portion of the elongate electrical connector.

* * * * *